United States Patent [19]
Böling

[11] Patent Number: 5,665,904
[45] Date of Patent: Sep. 9, 1997

[54] OSMOMETRIC DEVICE AND PROCESS FOR DETERMINING THE ANALYTE CONTENT OF A SOLUTION OF MIXED SUBSTANCES

[75] Inventor: Gerd Böling, Inden-Pier, Germany

[73] Assignee: Forschungszentrum Jülich GmbH, Jülich, Germany

[21] Appl. No.: 708,449

[22] Filed: Sep. 5, 1996

Related U.S. Application Data

[63] Continuation-in-part of PCT/DE95/00323, Mar. 6, 1995

[30]  Foreign Application Priority Data

Mar. 8, 1994 [DE] Germany .................. 44 07 637.1

[51] Int. Cl.$^6$ .................. G01N 7/10; G01N 13/04
[52] U.S. Cl. .................. 73/64.47; 73/61.41; 73/61.71; 210/85; 210/96.1; 210/90
[58] Field of Search .................. 73/64.47, 61.41, 73/61.43, 61.44, 61.71; 210/85, 90, 96.1, 96.2

[56] References Cited

U.S. PATENT DOCUMENTS

| | | | |
|---|---|---|---|
| 3,248,932 | 5/1966 | Bohrer | 73/53 |
| 3,866,460 | 2/1975 | Pearce et al. | 73/19 |
| 4,256,108 | 3/1981 | Theeuwes | 128/260 |
| 4,481,808 | 11/1984 | Sakata et al. | 73/61.1 R |
| 4,664,808 | 5/1987 | Kim | 210/638 |
| 4,891,968 | 1/1990 | Steudle et al. | 73/64.3 |
| 5,005,403 | 4/1991 | Steudle et al. | 73/64.3 |
| 5,141,873 | 8/1992 | Steudle et al. | 436/148 |
| 5,388,449 | 2/1995 | LeVeen et al. | 73/64.47 |

Primary Examiner—Hezron E. Williams
Assistant Examiner—J. David Wiggins
Attorney, Agent, or Firm—Klaus J. Bach

[57] ABSTRACT

In an osmometric measurement device and a method for determining the content of an analyte in a solution of a mixture of substances including the analyte, the mixture solution is admitted to a conduit of an osmotic cell structure having inner and outer cells filled with an osmoticum and divided by an inner membrane which is impermeable for an analyte in the outer cell and the outer cell is separated from the conduit by an outer membrane which is permeable for the analyte but not for other substances in the solution so that the pressure generated in the inner cell is only the result of the amount of analyte permeated into the outer cell and the pressure in the inner cell is determined by a pressure measuring device in pressure transmitting communication with the inner cell and is utilized for determining the content of the analyte in the solution of substances.

4 Claims, 3 Drawing Sheets

OSMOMETRIC DEVICE AND PROCESS FOR DETERMINING THE ANALYTE CONTENT OF A SOLUTION OF MIXED SUBSTANCES

This is a continuation-in-part application of International Application PCT/DE95/00323 filed Mar. 6, 1995 and claiming the priority of German Application P44 07 637.1 filed Mar. 8, 1994.

BACKGROUND OF THE INVENTION

The invention resides in an osmometric device for determining the analyte content of a solution of mixed substances which includes an osmotic cell consisting of a rigid wall and a membrane and provided with a pressure measurement device. The invention also resides in a method of determining the analyte content of a solution of mixed substances using the osmometric device.

Such measuring devices and methods are known for example from DE-OS 35 25 668 and also from the European parent 0 183 072. The measuring head of the known measuring device includes an osmotic membrane which has such a retention capability for substances that at least one of the substances in the mixture of substances in solution to be measured is capable of permeating the membrane and another is not.

Upon performing the known method, the pressure distribution as shown in FIG. 1 occurs in the osmotic cell of the measuring head which pressure is determined by a hydrostatic pressure sensing device comprising a resilient membrane and a force sensor. For determining the pressure, first an operating pressure $P_0$ is established by bringing a suitable solution (solvent) into contact with the osmometer solution by way of the osmotic membrane. Then the solution of the substance mixture is brought into contact with the osmotic membrane whereby, within a relatively short time $T_{min}$, the minimum pressure $P_{min}$ is established as the solvent of the osmotic cell permeates rapidly through the membrane outwardly. In time, the final pressure $P_E$ is established because the substances for which the membrane is permeable permeate at a slower rate. For determining the content of the substances, the pressure values $P_0$, $P_{min}$, and $P_e$ are utilized.

As the pressure curve shown in FIG. 1 indicates, the known methods require a measuring time of at least 30 minutes. There is also a regeneration period which is correspondingly long.

In practice, such a time was found to be too long. This is particularly true for on-line measurements for example during surveillance of a manufacturing process such as the production of beer.

It is the object of the present invention to provide an osmometric measuring device which permits determination of the analyte (the substance of interest) content of a solution of a substance mixture in a relatively short time and a correspondingly fast method of determining such analyte content.

SUMMARY OF THE INVENTION

In an osmometric measurement device and a method for determining the content of an analyte in a solution of a mixture of substances including the analyte, the mixture solution is admitted to a conduit of an osmotic cell structure having inner and outer cells filled with an osmoticum and divided by an inner membrane which is impermeable for an analyte in the outer cell and the outer cell is separated from the conduit by an outer membrane which is permeable for the analyte but not for other substances in the solution so that the pressure generated in the inner cell is only the result of the amount of analyte permeated into the outer cell and the pressure in the inner cell is determined by a pressure measuring device in pressure transmitting communication with the inner cell and is utilized for determining the content of the analyte in the solution of substances.

With the osmometric measuring device according to the invention, which includes a two chamber measuring cell structure, only the analyte for which the outer membrane does not represent a barrier—with the selection of suitable membranes—enters the measuring (outer) cell whereas the other substances which are of no interest or which disturb the procedure do not enter the measuring cell. The analyte content in the outer cell is determined on the basis of the pressure change in the inner cell which is rapidly established by the fast flow of fluid out of the inner cell depending on the analyte amount present in the outer cell.

In this regard the following comments made; "Analyte-impermeable" means that the retention capability of the membrane with regard to the analyte is so large that its passage through the membrane as compared to the passage of the solvent through the membrane is so delayed that during the exchange phase a relatively large amount of solvent passes while only little of the analyte passes through the membrane.

In the same way, "analyte-permeable but impermeable for the other substances of the mixture of substances" means that passage of the other substances through the outer membrane is so delayed that during passage of the permeable analyte through the outer membrane no noticeable amount of the substance for which the membrane is impermeable passes through the outer membrane; or: The speed constant for the analyte compared to that of the other substances is sufficiently large that essentially no other substances will pass through the membrane during the measurement procedure.

This means on the other hand that, with a given membrane, a substance (analyte) is considered to be able to permeate in the sense of the teachings of the present invention if, during the measurement procedure, it is substantially faster to permeate than the other substances in the solution, even though its permeance through the given membrane is delayed as compared to the pure solvent.

During use of the osmometric measuring device according to the invention, it is appropriate to first admit a suitable solution (solvent) to the conduit adjacent the outer membrane (b) for adjusting the operating pressure and then admit the solution of the mixture of substances including the analyte. The content of the analyte in the solution of the substance mixture is then determined from the hydrostatic pressure change which develops in the inner osmotic cell (A) as a result of the permeation of the analyte into the outer cell (B) ahead of the inner osmotic cell A.

The measuring device according to the invention and the method can be used for example to determine the alcohol content of beer. If, after adjustment of the operating pressure, beer is brought via the outer conduit into contact with the outer membrane of the two-chamber measuring cell, alcohol and water rapidly permeate the outer membrane and enter the outer osmotic cell (A) without delay. But no, or almost no, alcohol will enter the inner cell (B). At the same time, water flows, in accordance with the reverse osmosis principle, at a high rate from the inner cell (A) into the outer cell (B). The hydrostatic pressure difference which develops thereby and which is measured by a pressure sensing device is a measure for the alcohol content. In this procedure, it is not necessary to wait for, and measure, the particle flow, that is the permeation of the-alcohol through the inner membrane into the inner cell (A).

In an advantageous embodiment of the method according to the invention a regeneration phase is initiated immediately after the hydrostatic pressure change has been determined by exchanging the solution of the substance mixture present in the conduit by a suitable solution (solvent) for adjusting the operating pressure.

Since the determination of the analyte already present on the basis of a pure "water phase" requires only little time, little time is also needed for the regeneration phase wherein only water or solvent, respectively, flows back into the inner osmotic cell (A).

The analyte content can also be established by determining the hydrostatic pressure change over time as it develops in the inner cell (A) because of the permeation of the analyte into the outer cell (B). The pressure change over time findings are then utilized to determine the analyte content in the solution of the mixture of substances.

The invention will be described below on the basis of the accompanying drawings.

DESCRIPTION OF A PREFERRED EMBODIMENT

Figure 1:
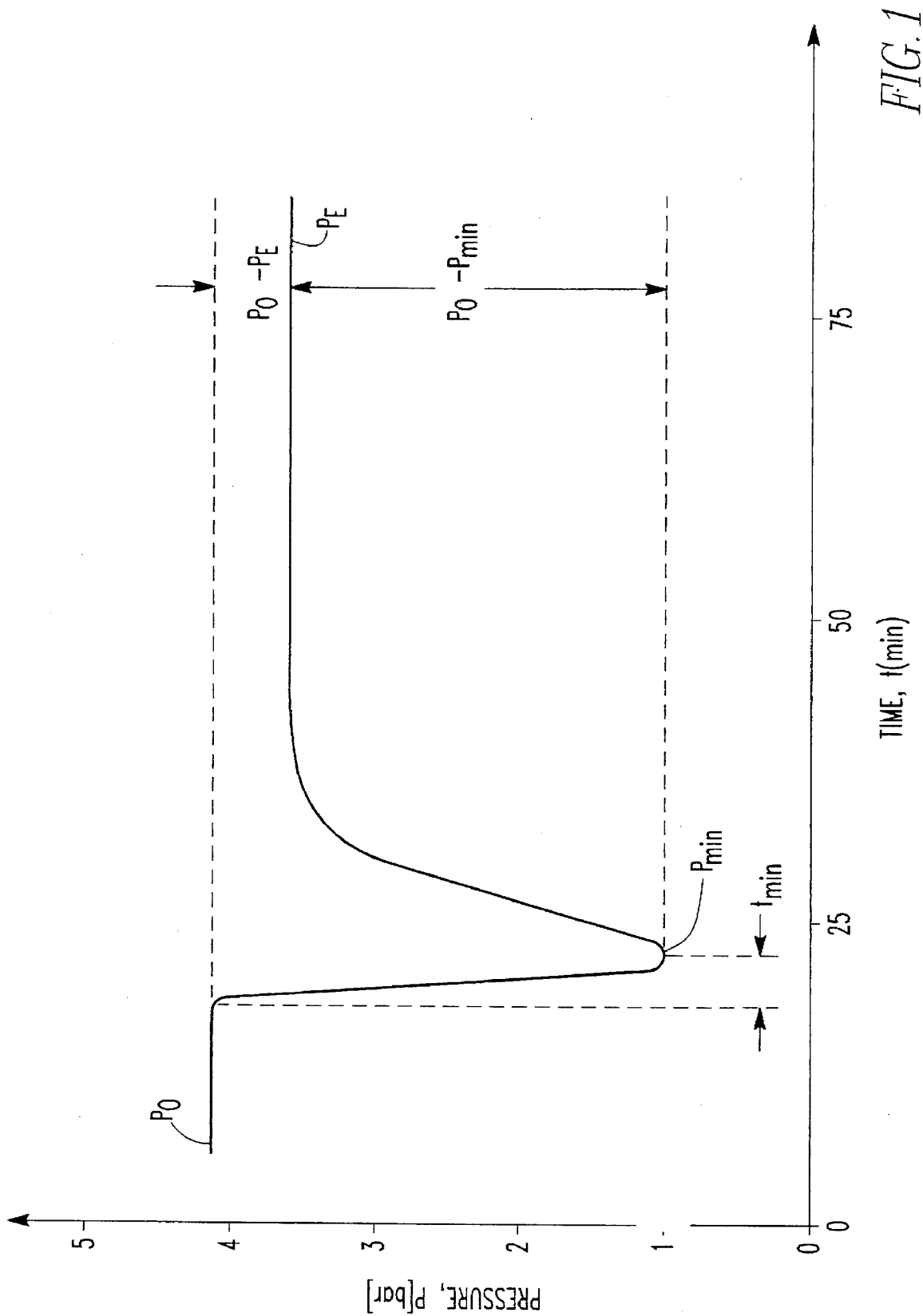
FIG. 1 is a graph showing pressure over time in a prior art osmometer.

The pressure distribution as represented in FIG. 1 relates to prior art devices and has been discussed earlier.

Figure 2:
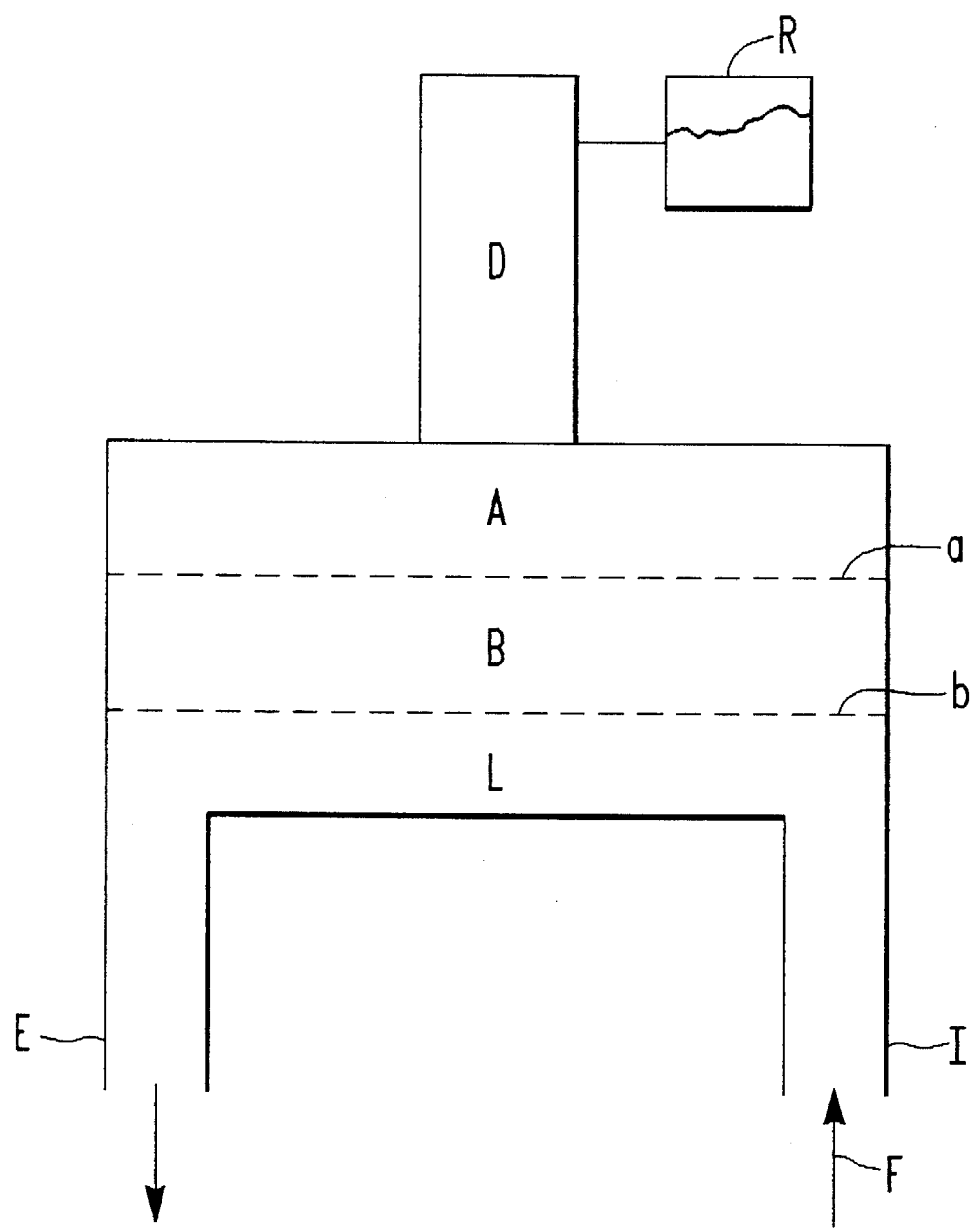
FIG. 2 is a schematic representation of the osmometric device according to the invention.

FIG. 2 shows a two-chamber osmotic cell system including an inner osmotic cell A and an outer osmotic cell B. The two cells are separated from one another by an inner membrane "a", that is they are in communication with one another by way of the inner membrane a. The osmotic cell B is disposed adjacent a fluid conduit structure L from which it is separated by an outer membrane b, that is, it is in communication with the fluid conduit structure L by way of the outer membrane b, which separates the outer cell B from the conduit L through which the solvent or, selectively, the substance mixture solution F passes. The fluid conduit structure has an output section E and an input section I in communication with a source supplying the solution with the analyte to the fluid conduit structure L for content analysis. A pressure measuring device D is arranged at the inner cell A to determine the pressure therein. It comprises a diaphragm type of a membrane which is exposed to the fluid pressure in the cell A and a pressure value recorder R for recording the pressure value determined by the pressure measuring device D.

Figure 3:
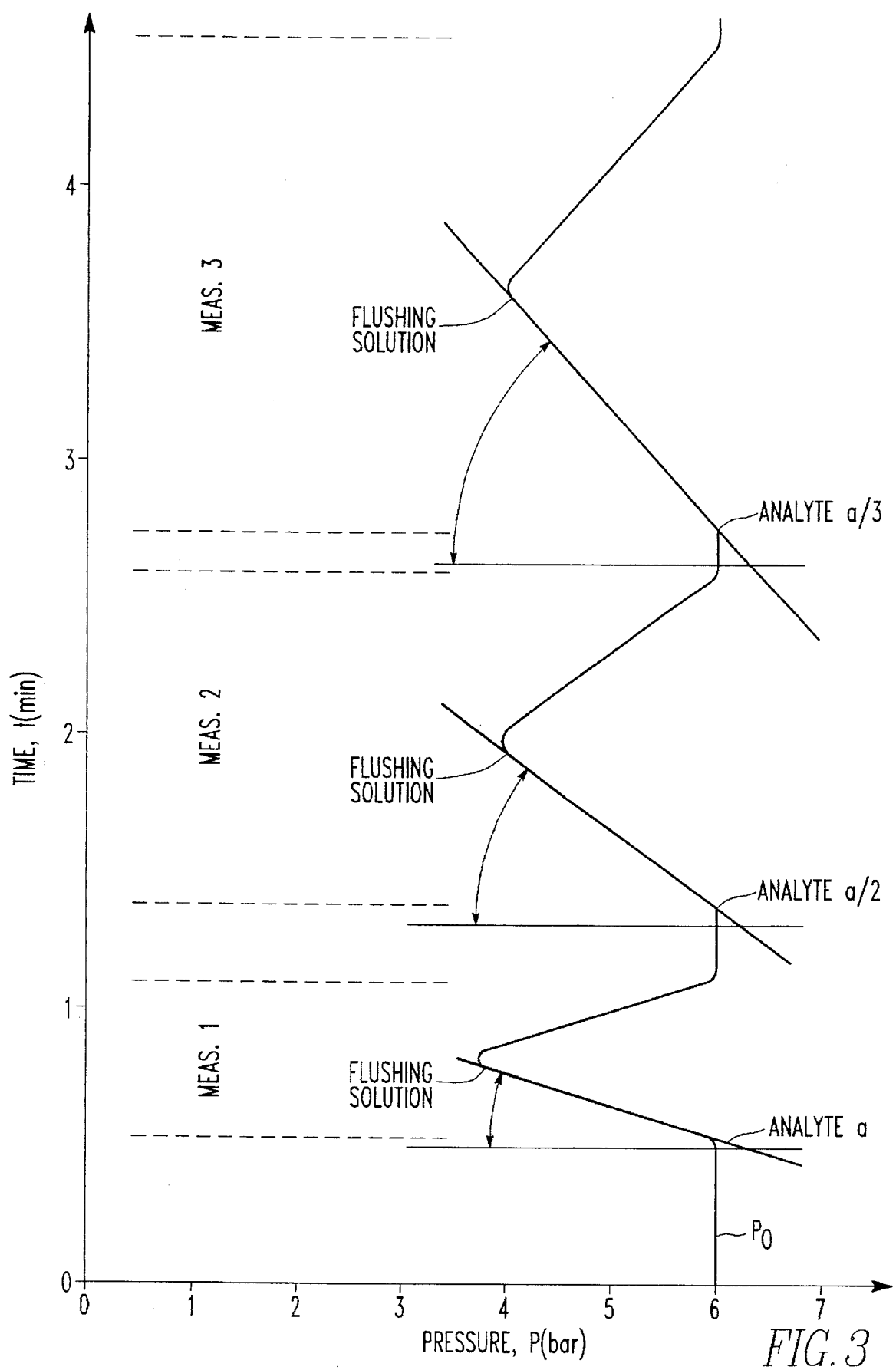
FIG. 3 shows the pressure distribution over time with the method according the invention.

FIG. 3 shows pressure distribution during three subsequent measurements. The solutions of the mixture of the substances, which, after flushing the system with a solvent, are subsequently supplied to the two-chamber osmotic system by way of the supply conduit L (see FIG. 2) are distinguished by the concentration of an analyte (for example, alcohol) in the solution. The first solution of the substance mixture has an analyte concentration a, the second solution has an analyte concentration a/2, and the third solution has an analyte concentration a/3.

As can be seen from FIG. 3, the initial inclination of the pressure/time curve decreases with each subsequent measurement, that is the initial inclination is essentially proportional to the concentration of the analyte in the mixture solution.

It is also apparent from FIG. 3 that the time required for the regeneration corresponds to the time required for the original pressure to be re-established. The regeneration phase begins when, instead of the substance mixture solution, a solution is conducted through the conduit L by which the operating pressure $P_0$ is established. This may be a pure solvent (for example water) (designated in FIG. 3 as flushing solution).

As can be further seen from FIG. 3, the measuring time for the first substance mixture solution is somewhat more than 0.6 min. (from about 0.5 to 1.1 min.), for the second substance mixture solution, it is about 1.3 minutes (from about 1.3 to 2.6 min.) and for the third substance mixture solution, it is about 1.9 min. (from about 2.8 to 4.7 min.).

Rapid and accurate measurement results are obtained with the osmometric device and the measurement method according to the invention as only the analyte enters the outer osmotic cell at a rate depending on its concentration in the solution of the mixture of substances, and the pressure sure in the inner osmotic cell rapidly adjusts to the concentration of the analyte in the outer osmotic cell.

The invention claimed is:

1. An osmotic measurement device for determining the content of an analyte in a solution of a mixture of substances including said analyte in a fluid flow subjected to chemical analysis, comprising an osmotic measurement structure having two distinct inner and outer osmotic cells separated by a rigid or rigidly supported membrane permitting the establishment of different operating pressures in said inner and outer osmotic cells, a pressure measuring device arranged in pressure transmitting communication with said inner osmotic cell for determining the fluid pressure therein and a fluid conduit structure disposed adjacent said outer osmotic cell and being separated therefrom by an outer osmotic membrane which is permeable for said analyte but impermeable for other substances in said solution, both said osmotic cells including an osmoticum with essentially the same osmolarity in the initial or, respectively, a regenerated basic state at a predetermined operating pressure where said fluid conduit structure has an input section and an output section that defines a fluid flow path connected in fluid communication with a source supplying said solution with said analyte for content analysis.

2. A method of determining the content of an analyte in an unassayed solution of a mixture of said analyte with at least one more substance in a fluid flow subject to chemical analysis using an osmometric measuring device including inner and outer osmotic cells separated by an inner rigid or rigidly supported membrane permitting the establishment of different pressures in said inner and outer osmotic cells and being impermeable for said analyte but permeable for an osmoticum in said cells, a pressure measuring device arranged in pressure transmitting communication with said inner cell for determining the pressure of said osmoticum therein and a fluid conduit structure disposed adjacent said outer osmotic cell and being separated therefrom by an outer osmotic membrane which is permeable for said analyte but impermeable for other substances in said unassayed solution, said osmotic cells including initially both the same osmoticum with the same osmolarity in an initial or regenerated basic state, said method comprising the steps of:

admitting to said fluid conduit structure, which extends along said outer membrane, first a solvent-type solution (containing substantially a chemical solvent) for establishing a certain operating pressure, then admitting to said fluid conduit structure said unassayed solution of said mixture of substances including said analyte to cause a resulting pressure over time distribution in said inner osmotic cell and determining from the hydrostatic pressure change measured in said inner osmotic cell as a result of the permeation of said analyte into said outer osmotic cell, the content of said analyte in said unassayed solution of said mixture of substances.

3. A method according to claim 2, wherein, immediately after determination of the hydrostatic pressure change in said inner osmotic cell, the unassayed solution of the mixture of substances in said fluid conduit structure is replaced by a suitable solution or solvent for readjusting the operating pressure in said osmotic cells towards said certain operating pressure in a regeneration phase which essentially restores said initial or regenerated basic state.

4. A method according to claim 2, wherein the pressure over time distribution, which is established from the measurement of the pressure developing in said inner cell as a result of the permeation of said analyte into said outer cell, is determined and the content of said analyte in said mixture solution is obtained therefrom.

* * * * *